United States Patent [19]

Goring

[11] 4,372,959

[45] Feb. 8, 1983

[54] 1-(5-OXOHEXYL)-3-ALKYL-7-(2-OXO-PROPYL)XANTHINES

[75] Inventor: Joachim E. Goring, Gronau, Fed. Rep. of Germany

[73] Assignee: Beecham-Wulfing GmbH & Co. KG, Fed. Rep. of Germany

[21] Appl. No.: 274,524

[22] Filed: Jun. 17, 1981

[30] Foreign Application Priority Data

Jun. 21, 1980 [GB] United Kingdom ................ 8020418

[51] Int. Cl.³ ..................... A61K 31/52; C07D 473/04
[52] U.S. Cl. .................................... 424/253; 544/271
[58] Field of Search ........................ 544/271; 424/253

[56] References Cited

U.S. PATENT DOCUMENTS

| 3,737,433 | 6/1973 | Mohler et al. | 424/253 |
| 4,225,607 | 9/1980 | Goring et al. | 424/253 |
| 4,242,345 | 12/1980 | Brenner et al. | 544/271 |
| 4,256,750 | 3/1981 | Goring et al. | 424/253 |
| 4,289,776 | 9/1981 | Mohler et al. | 424/253 |

FOREIGN PATENT DOCUMENTS 23032 1/1981 European Pat. Off. .
2330742 1/1975 Fed. Rep. of Germany .
1171968 2/1959 France .
7309709 1/1974 Netherlands .

OTHER PUBLICATIONS

Chem. Abst., 93, No. 11, (1980), p. 696, 204693h.

*Primary Examiner*—Paul M. Coughlan, Jr.
*Attorney, Agent, or Firm*—Jacobs & Jacobs

[57] ABSTRACT

Compounds of the formula (I):

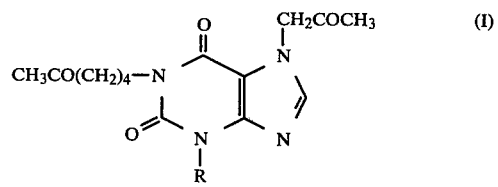

wherein R is $C_{1-4}$ alkyl, pharmaceutical compositions containing them and a process for their preparation. The compounds are useful for the treatment of peripheral vascular diseases in mammals.

6 Claims, No Drawings

1-(5-OXOHEXYL)-3-ALKYL-7-(2-OXOPROPYL)XANTHINES

This invention relates to compounds having useful pharmacological activity, to a process for their preparation and to pharmaceutical compositions containing them.

German Offenlegungsschrift No. 2,402,908 discloses that compounds of the formula (A):

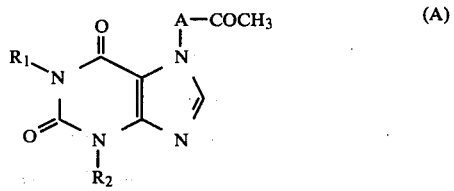

wherein $R_1$ and $R_2$, which may be the same or different, each represent a straight or branched-chain $C_{2-6}$ alkyl readical, or a cyclohexyl, alkoxyalkyl or hydroxyalkyl radical and A represents a hydrocarbon radical having up to 4 carbon atoms which may be substituted by a methyl group, are very effective in increasing the blood flow through skeletal muscle whilst at the same time showing low toxicity.

Netherlands Patent Application No. 7309709 discloses that compounds of the formula (A):

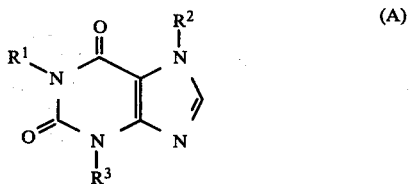

wherein at least one of $R^1$, $R^2$ and $R^3$ is oxoalkyl of 3 to 8 carbon atoms and each of the remaining variables is alkyl of 1 to 6 carbon atoms have a beneficial action on blood flow. 1-(5-oxohexyl)-3,7-dimethylxanthine is highlighted by reference, for its improvement of blood flow through inter alia muscle.

It has now been found that a specific narrow class of compounds within this broad general disclosure has surprisingly improved activity in increasing oxygen tension in ischaemic skeletal muscle relative to the same activity of 1-(5-oxohexyl)-3,7-dimethyl-xanthine.

The compounds also increase contractility in ischaemic skeletal muscle. These two properties effect an improvement in the metabolic status of the tissue which in turn makes the compounds of great potential use as agents for the treatment of peripheral vascular disease such as intermittent claudication.

Accordingly, the present invention provides the compounds of the formula (I):

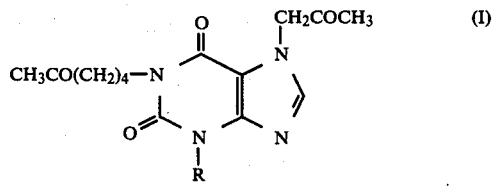

wherein R is $C_{1-4}$ alkyl.

R may be linear or branched $C_{1-4}$ alkyl. Suitable $C_{1-4}$ alkyl groups include methyl, ethyl, n-propyl, isopropyl and n-butyl. Two particularly suitable R $C_{1-4}$ alkyl groups are methyl and n-butyl.

From the foregoing it will be seen that two preferred compounds of the present invention are:

1-(5'-oxohexyl)-3-methyl-7-(2'-oxopropyl)xanthine
and 1-(5'-oxohexyl)-3-butyl-7-(2'-oxopropyl)xanthine.

The present invention also provides a process for the preparation of the compounds of the formula (I), which process comprises reacting a compound of the formula (II):

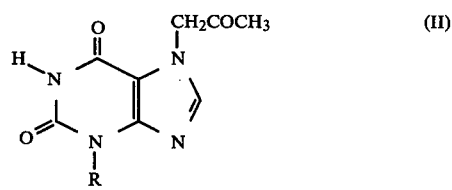

wherein R is as defined in formula (I), with a compound of the formula $Q-(CH_2)_4COCH_3$, wherein Q is an atom or group readily displaced by a nucleophile.

Suitable values of Q include chlorine, bromine and iodine atoms and activated ester groups, such as methanesulphonate and p-toluenesulphonate. Preferred values of Q include chlorine and bromine.

The reaction is generally effected in a polar organic solvent, such as a lower alkanol, acetone or dimethylformamide, or a mixture of such solvents. It is usually carried out in the presence of a moderate base. Suitable examples of such bases include inorganic bases, such as alkali metal or alkaline earth metal bases, for example the carbonates, such as potassium carbonate.

The reaction is generally carried out at atmospheric pressure and at a non-extreme temperature in the range from ambient to the boiling point of the reaction mixture.

The intermediates of the formula (II) may be prepared by reacting a compound of the formula (III):

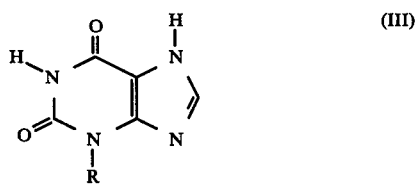

wherein R is as defined in formula (I) with a compound of the formula $CH_3COCH_2Q$ wherein Q is as hereinbefore defined, and is preferably chlorine or bromine. It is often necessary firstly to convert the compound of the formula (III) to an alkali metal salt at the 7-position, for instance the sodium salt. This may be carried out for example by treating the compound of the formula (III) with the corresponding alkali metal alkoxide. Under these conditions salification takes place selectively at the 7-position.

The acetonylation reaction is generally carried out in a polar organic solvent such as a lower alkanol or acetone at the reflux temperature of the reaction mixture and at atmospheric pressure.

Under these conditions acetonylation occurs selectively at the 7-position.

The compounds of this invention may be used to treat peripheral vascular disorders such as intermittent claudication. Thus the present invention also provides a pharmaceutical composition which comprises a compound of the formula (I) and a pharmaceutically acceptable carrier.

Although the compositions of this invention may be in a form suitable for parenteral administration by injection, it is preferred that the compositions are adapted for oral administration since this allows for more convenient administration. The compositions of this invention are most suitably provided in unit dose forms, for example as a tablet or capsule. Such dosage forms may, for example, contain 5 to 500 mgs or more usually from 10 to 200 mgs, for example from 15 to 150 mgs. Thus advantageously the unit dose composition of this invention may contain 15, 20, 25, 50, 75, 100 or 150 mgs or the like of the active agent. Such unit dosage forms are normally administered from 1 to 4 times daily in such a way that the daily dose for 1 70 kg adult will normally be in the range 40 to 1000 mgs and more usually from 50 to 900 mgs for example 60 to 800 mgs.

Particularly suitable unit dosage forms are tablets and capsules.

The composition of this invention may be formulated in conventional manner. Thus oral dosage units may contain such conventional agents as fillers (diluents), lubricants, binders distingrants, colurants, flavourings, surface active agents, preservatives, buffering agents and the like. Suitable fillers for use include cellulose, mannitol, lactose and other similar agents. Suitable disintengrants include starch, polyvinylpolypyrrolidone and starch derivatives such as sodium starch glycollate and the like. Suitable lubricants include stearic acid, magnesium stearate, magnesium lauryl sulphate and the like. Injectable compositions may consist essentially of a sterile, pyrogen free compound of this invention sealed into a vial optionally together with suspending and preserving agents. Such compositions may be made up for administration with sterile water or saline.

The compositions may be prepared by conventional methods of blending, filling, tabletting or the like.

The present invention also provides a method of treatment of peripheral vascular diseases in mammals, which method comprises administering to the sufferer a therapeutically effective amount of a compound of the formula (I).

The following Examples illustrate the preparation of the compounds of the present invention and the following Descriptions illustrate the preparation of intermediates therefor.

Description 1

3-methyl-7-(2'-oxopropyl)-xanthine (D1)

20,8 g pulverized 3-methylxanthine was added in portions to a freshly prepared solution of 2,86 g sodium in 125 ml absolute ethanol and heated under reflux to give the 3-methylxanthine sodium salt. 17,3 g chloroacetone in 125 ml absolute ethanol was then added dropwise, and the reaction mixture was heated under reflux for four hours. After cooling, the precipitate was filtered off and then dissolved in dilute aqueous sodium hydroxide solution.

To this alkaline solution hydrochloric acid was added dropwise with stirring to pH 11,5 (controlled by a pH meter). The precipitated 3-methyl-7-(2'-oxopropyl)-xanthine was filtered off under suction, and the residue was recrystallised from methanol/chloroform 1:1 to yield the product as a white powder.

Melting point: ≦295° C.

Yield: 8,1 g=29,2% of the theory

Elemental analysis:

|   | Calculated | Found |
|---|---|---|
| C | 48,65 | 48,60 |
| H | 4,54 | 4,53 |
| N | 25,21 | 25,08 |
| O | 21,60 | 21,61 |

The structure was confirmed by NMR spectroscopy.

Description 2

3-butyl-7-(2'-oxopropyl)-xanthine (D 2)

26,0 g pulverized 3-n-butylxanthine was added, stepwise, to a freshly prepared solution of 2,86 g sodium in 125 ml absolute ethanol, to give a clear solution. At a temperature of ca. 30° C., a solution of 17,3 g chloroacetone in 125 ml absolute ethanol was then added dropwise, with stirring. After two hours, the precipitated sodium chloride, together with the crude 3-butyl-7-(2'-oxopropyl)-xanthine, was filtered off by suction and the residue washed with absolute ethanol.

To remove the sodium chloride from this mixture, it was suspended in 700 ml of water, with stirring, for 30 min. The suspension was then filtered off by suction, and residue was dissolved in dilute aqueous sodium hydroxide solution.

To this alkaline solution, dilute hydrochloric acid was added dropwise with stirring to ca. pH 10. The precipitated 3-butyl-7-(2'-oxopropyl)-xanthine was filtered off under suction, and the residue was recrystallised from ethanol to yield the product as a white powder.

Melting point: 218° C.

Yield: 10,1 g ≙30,6% of the theory

Elemental analysis:

|   | Calculated | Found |
|---|---|---|
| C | 54,54 | 54,58 |
| H | 6,11 | 6,11 |
| N | 21,19 | 21,10 |
| O | 18,16 | 18,19 |

The structure was confirmed by NMR spectroscopy

EXAMPLE 1

1-(5'-oxohexyl)-3-methyl-7-(2'-oxopropyl)-xanthine(1)

3-methyl-7-(2'-oxopropyl)-xanthine (4,5 g) potassium carbonate (2,8 g) and dimethylformamide (34 ml) were stirred together and 1-bromhexan-5-one, freshly distilled, was added dropwise at room temperature. The mixture was then heated to 120° C. under a nitrogen stream for 30 min to completed the reaction. After cooling, the mixture was treated with water and extracted with chloroform several times. The chloroform phase was washed with water, dried over sodium sulphate and filtered, and the chloroform was removed in vacuo. The residue was recrystallised from ethanol to yield 1-(5'-oxohexyl)-5-methyl-7-(2'-oxopropyl)-xanthine as a white powder.

Melting point: 114° C.

Yield: 3,2 g ≙49,9% of the theory

Elemental analysis:

| | Calculated | Found |
|---|---|---|
| C | 56,24 | 56,15 |
| H | 6,29 | 6,25 |
| N | 17,49 | 17,61 |
| O | 19,98 | 20,06 |

The structure was confirmed by NMR spectroscopy.

1-(5'-oxohexyl)-3-butyl-7-(2'-oxopropyl)-xanthine (2)

3-butyl-7-(2'-oxopropyl)-xanthine (7,9 g), potassium carbonate (4,2 g) and dimethylformamide (51 ml) were stirred together and 1-bromhexane-5-one (8,1 g), freshly distilled, was added dropwise at room temperature. The mixture was then heated to 120°, under a stream of nitrogen, for 30 min. to complete the reaction. After cooling, the mixture was treated with ca. 100 ml of water and extracted several times with chloroform. The chloroform phase was washed with water, dried over sodium sulphate and filtered and the chloroform was removed in vacuo. The residue was recrystallised from ether to yield 1-(5'-oxohexyl)-3-butyl-7-(2'-oxopropyl)-xanthine.

Melting point: 87° C.
Yield: 7,4 g=68,0% of the theory

Elemental analysis:

| | Calculated | Found |
|---|---|---|
| C | 59,65 | 60,00 |
| H | 7,23 | 7,03 |
| N | 15,46 | 15,38 |
| O | 17,66 | 17,59 |

The structure was confirmed by NMR spectroscopy.

Pharmacological Data

Cats of both sexes were anaesthetized by i.p. injection of urethane/chloralose (120/60 mg/kg). The intraduodenal (i.d.) administration of compounds (as a suspension) was conducted by means of a plastic catheter which was inserted into the duodenum following midline incision at the abdominal cavity.

(i) Muscle surface $pO_2$-measurement

The skin above the measuring site (3-4 mm in diameter) was removed and one multiwire-surface electrode (Eschweiler, Kiel) was placed on the gastrocnemius muscle of each hind-limb. The femoral artery in one hindlimb was ligated in order to induce ischaemia. Muscle temperature was monitored by means of a thermocouple (Ellab, Copenhagen). The electrode current was measured every 6 to 8 s and collected for periods of 4 min (Hewlett-Packard programmable data logger system 3051 A). After each period, mean value and standard deviation were calculated.

This test method for measuring increased oxygen tension in skeletal muscle was used for the comparison testing of compounds 1 and 2 for their effect in increasing oxygen tension against 1-(5-oxohexyl)-3,7-dimethylxanthine (B) which is the only compound named in Netherlands Patent Application No. 7309709 for its pharmacological effect on blood in muscle. This latter compound is believed to be the compound in NL 7309709 structurally closest to the present compounds (ii) Skeletal muscle contractility After dissection of the skin of the calf muscles, the sciatic nerve was cut abovt 3 cm proximal to the knee. The tendon of the calf muscles was cut and connected to an isometric force transducer (SWEMA, SG 3). In order to maintain constant differences and a resting tension of 100 p in cats and 25 p in rats, the hindlimb was fixed at the tibia by means of a clamp. Direct stimulation of the muscles consisted of square wave pulses of 4 msec duration at a frequency of 2 Hz and at a voltage of 50 V in cats. In order to keep the muscles wet and at a normal temperature, the muscles were continously superfused with 0.9% w/v NaCl solution (38° C.). Femoral blood flow was restricted by a graded occlusion of the artery leading to a reduction of contractility by ca. 30%. After having reached a constant level of the contraction force, the appropriate vehicle (NaCl or Methocel) was injected, followed by the test substance.

Results (i) $pO_2$ in cat gastrocnemius - Comparison testing

| Compound | Dosage (mg/kg) i.d. | n | $C_s$* | Hypoxic Tissue $\overline{\Delta pO_2}$ | E |
|---|---|---|---|---|---|
| 1 | 0.8 | 3 | 1 | 2.0 | 2.0 |
| | 5.0 | 3 | 0.33 | 6.3 | 2.1 |
| | 12.5 | 3 | 1 | 2.5 | 2.5 |
| 2 | 2.0 | 3 | 1 | 8.2 | 8.2 |
| B | 5.0 | 23 | 0.46 | 2.29 | 1.05 |
| | 12.0 | 23 | 0.55 | 3.34 | 1.84 | n = no. of experiments = no. of measuring sites
*$C_s$ = Significance coefficient = number of experiments with significant $pO_2$ increases per total number of experiments $\overline{\Delta pO_2}$ = Mean $pO_2$ increases in experiments with significant $pO_2$ increases (Torr)

E = Efficiency-index = $C_s \times \overline{\Delta pO_2}$ (Torr)

(ii) Muscle contractility—Compound 1 in the cat

Contractility was increased by 17% at 12.5 mg/kg i.d. in 3 experiments.

Toxicity

No toxic effects were observed at the test dosages.

I claim:

1. A compound of the formula (I):

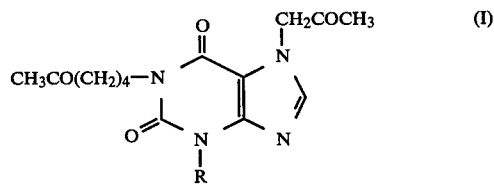

wherein R is alkyl of 1 to 4 carbon atoms.

2. A compound according to claim 1 wherein R is methyl or n-butyl.

3. 1-(5'-oxohexyl)-3-methyl-7-(2'-oxopropyl)xanthine.

4. 1-(5'-oxohexyl)-3-butyl-7-(2'-oxopropyl)xanthine.

5. A pharmaceutical composition for the treatment of peripheral vascular diseases in mammals, which comprises a therapeutically effective amount of a compound of claim 1 and a pharmaceutically acceptable carrier.

6. A method of treatment of peripheral vascular diseases in mammals, which method comprises administering to the sufferer a therapeutically effective amount of a compound of claim 1.

* * * * *